US011723915B2

(12) United States Patent
Albers et al.

(10) Patent No.: US 11,723,915 B2
(45) Date of Patent: *Aug. 15, 2023

(54) ENZYMATICALLY HYDROLYSED PECTIC POLYSACCHARIDES FOR TREATING OR PREVENTING INFECTIONS

(71) Applicant: NutriLeads B.V., Wageningen (NL)

(72) Inventors: Ruud Albers, Rockanje (NL); Maria Tzoumaki, Wageningen (NL)

(73) Assignee: NutriLeads B.V., Wageningen (NL)

( * ) Notice: Subject to any disclaimer, the term of this patent is extended or adjusted under 35 U.S.C. 154(b) by 355 days.

This patent is subject to a terminal disclaimer.

(21) Appl. No.: 16/855,568

(22) Filed: Apr. 22, 2020

(65) Prior Publication Data

US 2020/0246373 A1 Aug. 6, 2020

Related U.S. Application Data

(63) Continuation of application No. PCT/EP2018/079055, filed on Oct. 23, 2018.

(30) Foreign Application Priority Data

Oct. 23, 2017 (EP) ..................................... 17197706
Sep. 7, 2018 (WO) ................. PCT/EP2018/074127

(51) Int. Cl.
| | |
|---|---|
| A61K 31/732 | (2006.01) |
| A61P 31/00 | (2006.01) |
| A61K 31/715 | (2006.01) |
| A23L 29/00 | (2016.01) |
| C08B 37/00 | (2006.01) |
| C12N 9/10 | (2006.01) |

(52) U.S. Cl.
CPC ............ *A61K 31/732* (2013.01); *A23L 29/06* (2016.08); *A61K 31/715* (2013.01); *A61P 31/00* (2018.01); *C08B 37/0006* (2013.01); *C12N 9/1051* (2013.01); *C12Y 301/01011* (2013.01)

(58) Field of Classification Search
CPC ........................... A61K 31/715; A61K 31/732
See application file for complete search history.

(56) References Cited

U.S. PATENT DOCUMENTS

| | | |
|---|---|---|
| 2002/0022601 A1 | 2/2002 | Konno et al. |
| 2004/0072791 A1 | 4/2004 | Kunz et al. |
| 2010/0047209 A1 | 2/2010 | Stanton et al. |
| 2011/0112048 A1 | 5/2011 | Cox et al. |
| 2013/0137757 A1 | 5/2013 | Koide |
| 2014/0275233 A1 | 9/2014 | Heiman |
| 2014/0288021 A1 | 9/2014 | Freitas et al. |
| 2016/0151485 A1* | 6/2016 | Albers ................. A61K 31/715 424/278.1 |
| 2016/0250625 A1 | 9/2016 | Kanaya et al. |

FOREIGN PATENT DOCUMENTS

| | | |
|---|---|---|
| CN | 102784193 A | 11/2012 |
| KR | 10-2017-0053144 A | 5/2017 |
| WO | WO-01/76609 A1 | 10/2001 |
| WO | WO-2004/084652 A1 | 10/2004 |
| WO | WO-2005/095463 A1 | 10/2005 |

(Continued)

OTHER PUBLICATIONS

Bonnin, E. et al., Appl. Microbiol. Biotechnol., "Pectin-modifying enzymes and pectin-derived materials: applications and impacts", 2014, vol. 98, pp. 519-532 (Year: 2014).*
"Prevent" definition, WordNet Search 3.1; available atwordnetweb. princeton.edu/perl/webwn; last accessed Jan. 2021 (Year: 2021).*
"Common Cold", Mayo Clinic; available at https://www.mayoclinic. org/diseases-conditions/common-cold/symptoms-causes/syc-20351605; last accessed Jun. 2022 (Year: 2022).*
Broxterman Suzanne E et al: "Acetylated pectins in raw and heat processed carrots", Carbohydrate Polymers, vol. 177, Aug. 30, 2017 (Aug. 30, 2017), pp. 58-66, XP085205714, ISSN: 0144-8617, DOI: 10.1016/J.CARBPOL.2017.08.118.

(Continued)

*Primary Examiner* — Bahar Craigo
(74) *Attorney, Agent, or Firm* — Foley & Lardner LLP (57) ABSTRACT

The invention relates to a product for use in the therapeutic or prophylactic treatment of infections, said treatment comprising oral administration of the product, wherein the product is selected from a nutritional formulation, a food product, a dietary supplement, a beverage and a pharmaceutical product, said product containing carrot RG-I polysaccharides having the following combination features:
  a molecular weight in the range 10-300 kDa;
  a backbone consisting of galacturonic acid residues and rhamnose residues, said rhamnose residues being contained in alpha(1→4)-galacturonic-alpha(1→2)-rhamnose residues;
  the following monosaccharide composition:
    20-60 mol. % galacturonic acid residues, wherein the individual galacturonic acids can be methylated and/or acetyl-esterified;
    8-50 mol. % rhamnose residues;
    0-40 mol. % arabinose residues;
    0-40 mol. % galactose residues;
    molar ratio of galacturonic acid residues to rhamnose residues in the range of 5:1 to 1:1;
    galacturonic acid residues, rhamnose residues, arabinose residues and galactose residues together constitute at least 85 mol. % of the monosaccharide residues in the carrot RG-I polysaccharides.
These carrot RG-I polysaccharides can be produced by partially hydrolysing pectic polysaccharides present in a carrot pectin isolate. The effectiveness of carrot RG-I polysaccharides against infections is substantially improved by enzymatically hydrolysing the RG-I polysaccharides to remove at least part of the homogalacturonan component.

9 Claims, 3 Drawing Sheets

(56) References Cited

FOREIGN PATENT DOCUMENTS

| WO | WO-2011/069781 A1 | 6/2011 |
|---|---|---|
| WO | WO-2011/136634 A1 | 11/2011 |
| WO | WO-2012/148277 A1 | 11/2012 |
| WO | WO-2015/192247 A1 | 12/2015 |
| WO | WO-2016/132130 A1 | 8/2016 |

OTHER PUBLICATIONS

International Search Report dated Jan. 4, 2019 received in corresponding International Application No. PCT/EP2018/079055, 5 pages.
International Search Report dated Jan. 4, 2019 received in corresponding International Application No. PCT/EP2018/079058, 5 pages.
Kirtschev[Kirchev] N A et al: "Pectins of some carrot (*Daucus carota*) varieties, (translated) TIOL—Ueber Pektinstoffeeiniger Vertreter der Art "Daucus Carota". ". Zeitschrift Fuer Lebensmittel-Untersuchung Und-Forschung, vol. 170, No. 1, 1980, pp. 31-33, XP002776946.
Merve Kaya et al: "Characterization of citrus pectin samples extracted under different conditions: influence of acid type and pH of extraction", Annals of Botany., vol. 114, No. 6, Jul. 31, 2014 (Jul. 31, 2014), pp. 1319-1326, XP055535664, GB ISSN: 0305-7364, DOI: 10.1093/aob/mcu150.
Morris GA et al: "Physical characterisation of the rhamnogalacturonan and homogalacturonan fractions of sugar beet (*Beta vulgaris*) pectin", Carbohydrate Polymers, Applied Science Publishers, Ltd. Barking, GB, vol. 82, No. 4, Nov. 11, 2010 (Nov. 11, 2010), pp. 1161-1167, XP027266305, ISSN: 0144-8617 [retrieved on Sep. 7, 2010] paragraphs [02.2], [03.5]; example fig. 1.
Nastaran Khodaei et al: "Extraction and structural characterisation of rhamnogalacturonan I-type pectic polysaccharides from potato cell wall", Food Chemistry, vol. 139, No. 1-4, Feb. 10, 2013 (Feb. 10, 2013), pp. 617-623, XP55244701, NL ISSN: 0308-8146, DOI: 10.1016/j.foodchem.2013.01.110 paragraphs [02.1], [2.2.1], [2.2.2], [03.1], [03.2], [03.3], [03.4], [0004].
Park Hye-Ryung et al: "Structural 1-12, elucidation of anti-metastatic 14-20 rhamnogalacturonan I I from the pectinase digest of citrus peels (*Citrus unshiu*)", International Journal of Biological Macromolecules, Els Ev I Er Bv, NL, vol. 94, Sep. 29, 2016 (Sep. 29, 2016), pp. 161-169, XP029818798, ISSN: 0141-8130, DOI: 10.1016/J.IJBIOMAC.2016.09.100 paragraphs [0001], [02. 1], [02. 2], [03. 1]; figure 1.
Ridley B L et al: "Pectins: structure, biosynthesis, and oligogalacturonide-related signaling", Phytochemi, Pergamon Press, GB, vol. 57, No. 6, Jul. 1, 2001 (Jul. 1, 2001), pp. 929-967, XP004245805, ISSN: 0031-9422, DOI:10.1016/S0031-9422(01)00113-3.
Alaa Abdul Aziz: "The effect of the Capsicum annuum in the diet of broilers on the isolation and shedding rate of *Salmonella paratyphoid*." Al-Qadssiya University ,Vet. Med. Coll. Kufa Journal for Veterinary Medical sciences, vol.(1), No. (1,2010.
Anne Petersen et al: "Some putative prebiotics increase the severity of *Salmonella enterica* serovar Typhimurium infection in mice", BMC Microbiology 2009, 9:245, Nov. 30, 2009.
Babbar et al., "Pectic oligosaccharides from agricultural by-products: production, characterization and health benefits", Critical Reviews in Biotechnology, vol. 36, No. 4, 2015, pp. 594-606.
Bryony N. Parsons et al: "Dietary Supplementation with Soluble Plantain Non-Starch Polysaccharides Inhibits Intestinal Invasion of *Salmonella typhimurium* in the Chicken". PLOS One, vol. 9, No. 2, Feb. 3, 2014 (Feb. 3, 2014), p. e87658, XP055496849,DOI: 10.1371/journal.pone.0087658 the whole document.
Chatterjee et al., "Effect of Fruit Pectin on Growth of Lactic Acid Bacteria", Journal of Probiotics & Health, vol. 4, No. 2, 2016 (6 pages).
De Weirdt et al., "Human faecal microbiota display variable patterns of glycerol metabolism", FEMS Microbiology Ecology, vol. 74, 2010, pp. 601-611 (11 pages).
Edgar, "Search and clustering orders of magnitude faster than BLAST", Bioinformatics, vol. 26, No. 19, 2010, pp. 2460-2461 (2 pages).
Gomez et al. "Prebiotic potential of pectins and pectic oligosaccharides derived from lemon peel wastes and sugar beet pulp: A comparative evaluation", Journal of Functional Foods, vol. 20, 2016, pp. 108-121 (14 pages).
Gregory et al. "QTIME allows analysis of high-throughput community sequencing data" Nature Methods, vol. 7, No. 5, 2010, pp. 335-336 (4 pages).
International Search Report issued for PCT Appl. Ser. No. PCT/EP2018/074127 dated Dec. 11, 2018 (4 pages).
Khodaei et al., "Enzymatic extraction of galactan-rich rhamnogalacturonan I from potato cell wall by-product", LWT—ood Science and Technology, vol. 57, 2014, pp. 207-216 (10 pages).
Kim et al., "Effect of arabinoxylan- and rhamnogalacturonan I-rich polysaccharides isolated from young barley leaf on intestinal immunostimulatory activity", Journal of Functional Foods, vol. 35, 2017, pp. 384-390 (7 pages).
Reeves, et al. "AIN-93 Purified Diets for Laboratory Rodents: Final Report of the American Institute of Nutrition Ad Hoc Writing Committee on the Reformulation of the AIN-76A Rodent Diet" Journal of Nutrition, vol. 123, No. 11, 1993, pp. 1939-1951 (15 pages).

* cited by examiner

ENZYMATICALLY HYDROLYSED PECTIC POLYSACCHARIDES FOR TREATING OR PREVENTING INFECTIONS

CROSS-REFERENCE TO RELATED APPLICATIONS

This application is a continuation of International Application No. PCT/EP2018/079055, filed Oct. 23, 2018, which application claims priority to European application No. 17197706.9, filed Oct. 23, 2017 and International Application No. PCT/EP2018/074127 filed Sep. 7, 2018, all of which are hereby incorporated by reference herein in their entireties.

TECHNICAL FIELD OF THE INVENTION

The present invention relates to the use of an enzymatically hydrolysed pectic polysaccharides in the prophylactic or therapeutic treatment of infections, such as infections of the upper respiratory tract. The enzymatically hydrolysed pectic polysaccharides originate from carrot and are characterised by a very high rhamnogalacturonan I (RG-I) content.

More particularly, the invention provides a product selected from a nutritional formulation, a food product, a dietary supplement, a beverage or a pharmaceutical product, said product containing the aforementioned enzymatically hydrolysed carrot RG-I polysaccharides. The invention further relates to the use of the aforementioned product in the treatment of infections and to a process of preparing the enzymatically hydrolysed carrot RG-I polysaccharides.

BACKGROUND OF THE INVENTION

Infection is the invasion of an organism's body tissues by disease-causing agents, their multiplication, and the reaction of host tissues to these organisms and the toxins they produce. Organisms can fight infections using their immune system. The immune system is a host defence system comprising many biological structures and processes within an organism that protects against disease. Nutrition is a critical modulator of immune function. Dietary fibres, for instance, can modulate various properties of the immune system and thus modify resistance to infections. Stimulating or supporting the immune system results in more effective immune responses to disease-causing organisms. This can result in the prevention of symptomatic infections or lead to faster recovery of infections.

Upper respiratory tract infections are illnesses caused by an acute infection which involves the upper respiratory tract including the nose, sinuses, pharynx or larynx. This commonly includes nasal obstruction, sore throat, tonsillitis, pharyngitis, laryngitis, sinusitis, otitis media, certain types of influenza and the common cold. Most infections are viral in nature and in other instances the cause is bacterial. Upper respiratory tract infections can also be fungal or helminth in origin, but these are far less common. Lower respiratory tract infections are generally more serious than upper respiratory infections and are the leading cause of death among all infectious diseases.

Viruses that can cause acute respiratory tract infections include rhinoviruses, influenza viruses, adenoviruses, coxsackie virus, parainfluenza virus, respiratory syncytial viruses and human metapneumovirus. Bacteria that can cause upper respiratory infections include group A beta-hemolytic streptococci, *Corynebacterium diphtheriae*, *Neisseria gonorrhoeae*, *Chlamydia pneumoniae*, group C beta-hemolytic streptococci.

Children have 2-9 viral respiratory illnesses per year. Upper respiratory tract infections are the leading reasons for people missing work and school. Vaccination against influenza viruses, adenoviruses, measles, rubella, *Streptococcus pneumoniae, Haemophilus influenzae*, diphtheria, *Bacillus anthracis*, and *Bordetella pertussis* may prevent them from infecting the URT or reduce the severity of the infection.

Other infections for which the immune system provides protection include intestinal infections. Intestinal infectious diseases include cholera, typhoid fever, paratyphoid fever, other types of salmonella infections, shigellosis, botulism, gastroenteritis, and amoebiasis among others. Gastroenteritis, also known as infectious diarrhea, is inflammation of the gastrointestinal tract that involves the stomach and small intestine. Signs and symptoms include some combination of diarrhea, vomiting, and abdominal pain. Fever, lack of energy, and dehydration may also occur. Gastroenteritis can be due to infections by viruses, bacteria, parasites, and fungus. Rotavirus, norovirus, adenovirus, and astrovirus are known to cause viral gastroenteritis. Rotavirus is the most common cause of gastroenteritis in children.

In the developed world *Campylobacter jejuni* is the primary cause of bacterial gastroenteritis. Other bacteria that can cause gastroenteritis include *Escherichia coli, Salmonella, Shigella, Staphylococcus aureus* and *Campylobacter* species. Toxigenic *Clostridium difficile* is an important cause of diarrhea that occurs more often in the elderly. A number of protozoa can also cause gastroenteritis most commonly *Giardia lamblia*, but *Entamoeba histoiytica, Cryptosporidium* spp., and other species have also been implicated.

US 2004/072791 describes the use of pectin hydrolysis products for blocking the attachment of harmful substances or organisms to mammalian cells, in particularly for fighting infections. The pectin may be obtained from citrus, apple or sugar beet.

US 2002/0022601 describes a method for preventing or treating common cold, comprising administering an agent comprising at least one component selected from chitin oligosaccharide, chitosan oligosaccharide and partially deacetylated chitin oligosaccharide.

US 2011/0112048 describes a method of reducing upper respiratory tract infection symptoms in stressed subjects, the method comprising: administering an effective amount of beta-glucan.

US 2013/0137757 describes a method of inhibiting influenza virus infection, the method comprising: treating a composition mainly containing pectin and polynucleotide to a mucous membrane of the subject to inhibit adhesion between hemagglutinin of influenza virus and sialic acid.

US 2014/0288021 describes the use of arabinogalactan and polyphenols from larch trees in prophylactic treatment of upper respiratory tract infections.

US 2016/0250625 describes a method for treatment of an upper respiratory tract infection, the method comprising administering to a composition comprising non-replicating probiotic micro-organisms selected from the group consisting of Bifidobacteria, Lactobacilli, Propionibacteria, and combinations thereof.

Pectin is a structural hetero polysaccharide that is present in the primary cell walls of terrestrial plants.

Pectic polysaccharides are a heterogeneous group of polysaccharides comprising varying amounts of the following polysaccharide components:

(i) homogalacturonan (HG),
(ii) xylogalacturonan (XG),
(iii) apiogalacturonan (AG),
(iv) rhamnogalacturonan-I (RG-I), and
(v) rhamnogalacturonan-II (RG-II).

Figure 1:
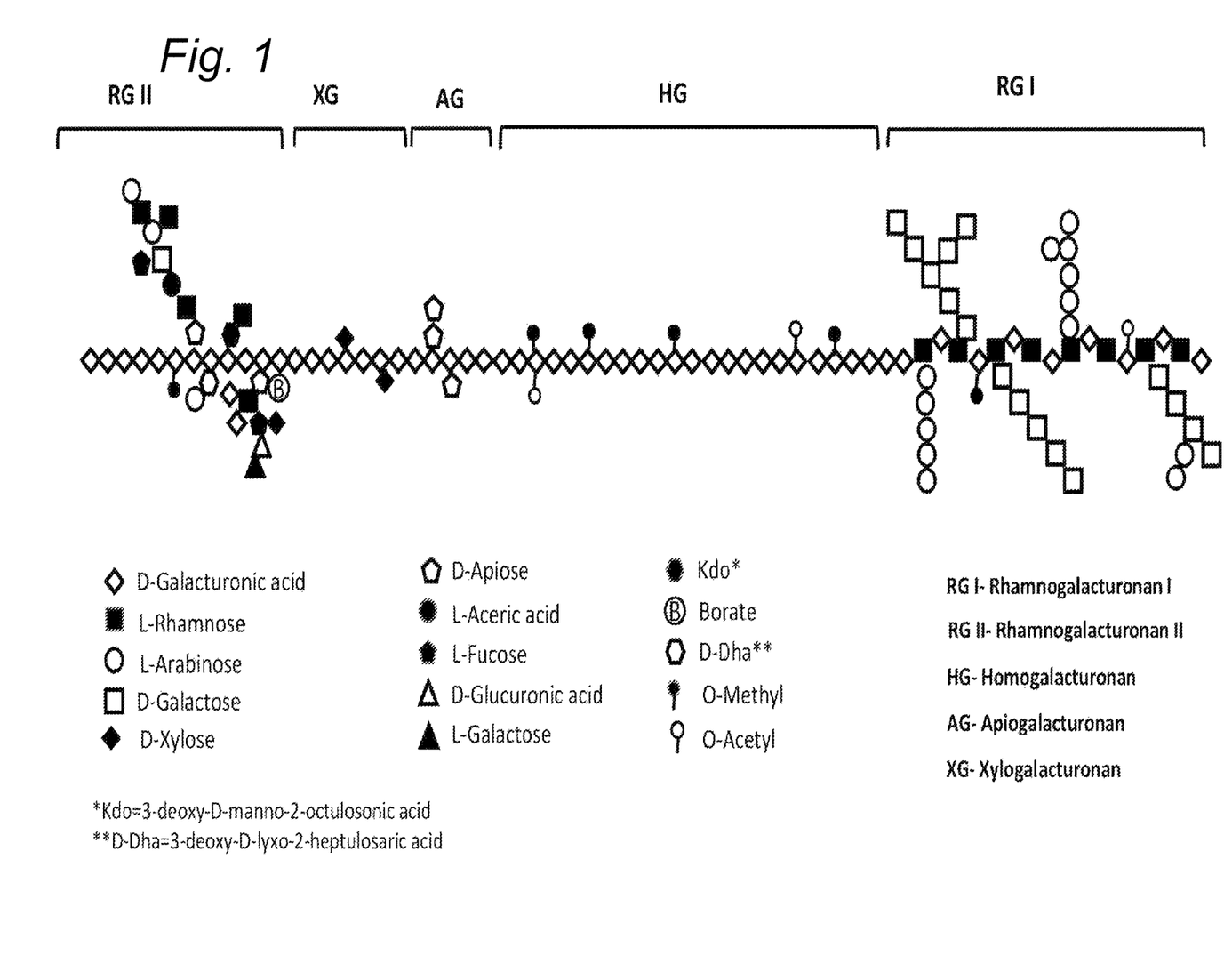
FIG. 1 provides a schematic representation of the structure of pectic polysaccharides, including the aforementioned 5 polysaccharide components.

FIG. 1 provides a schematic representation of the structure of pectic polysaccharides, including the aforementioned 5 polysaccharide components. It is noted that the polysaccharide components AG, XG and RG-II typically represent only a minor fraction of pectic polysaccharides.

The polysaccharide components HG, AG, XG and RG-II each comprise a backbone that consists of a linear chain of α-(1→4)-linked D-galacturonic acid monosaccharide units.

Figure 2:
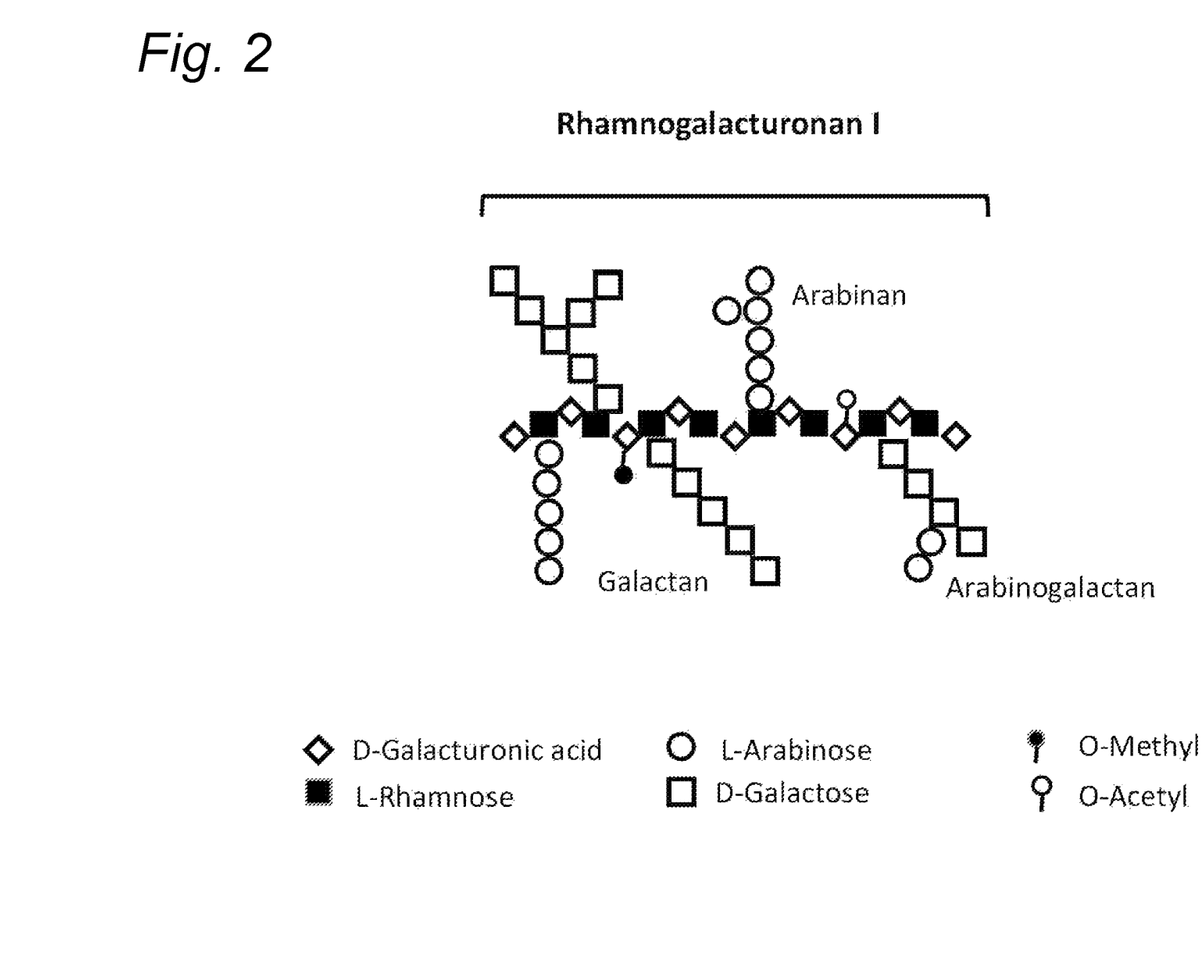
FIG. 2 provides a schematic representation of the structure of RG-I comprising a backbone that consists of a linear chain of the repeating disaccharide units: 4)-α-D-galacturonic acid-(1,2)-α-L-rhamnose-(1.

Only RG-I comprises a backbone that consists of a linear chain of the repeating disaccharide units: 4)-α-D-galacturonic acid-(1,2)-α-L-rhamnose-(1. A schematic representation of the structure of RG-I is shown in FIG. 2.

Pectic polysaccharide composition and fine structure vary widely depending on the plant source and the extraction conditions applied. The homogalacturonan domain can have a length of up to about 100 consecutive D-GalA residues. The RG-I domain containing the side chains is usually called the 'ramified region' or 'hairy region', while the homogalacturonan domain (connected to RG-I domains) is not typically substituted with glycosides or glycosidic side chain.

The GalA residues in RG-I are linked to the Rha residues via the 1 and 4 positions, while the Rha residue is linked to the GalA residue via the anomeric and 2-OH positions. In general about 20-80% of the Rha residues is branched at the 4-OH position (depending on the plant source and the method of isolation), with neutral and acidic side chains. These side chains consist mainly of Ara and Gal residues linked in various manners, constituting polymers known as arabinans, arabinogalactan I (AG-I) and/or AG-II. AG I is composed of a beta-(1,4)-linked D-Gal backbone with substitutions at 3-OH of alpha-L-arabinosyl groups; the Gal backbone can have interspacing alpha(1,5)-L-Ara units. AG-II consists of highly ramified galactan with predominantly interior beta(1,3)-linked D-Gal with substitutions of short (1,6)-linked chains exteriorly. The latter has further attachments of (1,3)- and/or alpha(1,5)-linked L-Ara. The oligosaccharide side chains may be linear or branched, and some of these side chains may be terminated with alpha-L-fucosides, beta-D-glucuronides, and 4-O-methyl beta-D-glucuronyl residues.

WO 2011/069781 describes edible products comprising a polysaccharide obtained from plants of the species *Camellia sinensis*, wherein the backbone of the polysaccharide comprises alternating rhamnogalacturonan-I cores and alpha(1,4)-linked polygalacturonic acid or alpha(1,4)-linked oligogalacturonic acid cores, wherein the molar ratio of galacturonyl acid residues to rhamnosyl residues in the backbone of the polysaccharide ranges from 2.5:1 to 1:1, and wherein the polysaccharide has a molecular weight of at least 70 kDa. The edible products may additionally contain polysaccharides that are obtainable from one or more plants belonging to the Apiaceae family, preferably from plants of the species *Daucus carota* (carrot). Table 1 describes a pectic polysaccharide fraction isolated from carrot having a molecular weight of more than 110 kDa. Table 2 shows that this polysaccharide fraction had in vitro immune modulating activity.

WO 2012/148277 describes a preparation having a dry matter content of at least 20 wt. %, said preparation containing at least 50% by weight of dry matter of a mixture of pectic polysaccharides, including at least 20%, calculated by weight of the pectic polysaccharides, of rhamnogalacturonan-I pectins having a molecular weight of more than 40 kDa, said mixture of pectic polysaccharides being characterized by:
a degree of methylation of the galacturonyl acid residues of not more than 20%;
a degree of acetylation of the galacturonyl acid residues of not more 20%; wherein the preparation does not form a gel when it is diluted with an aqueous solution of 50 mM ammoniumbicarbonate to a solids content of 2.5 wt. %. The examples describe pectic polysaccharide fractions that were isolated from carrot, using different extraction procedures. Some of these fractions were found to have immunomodulating activity.

WO 2004/084652 describes a process for producing a vegetable puree, comprising the sequential steps of:
a) crushing, chopping or slicing the vegetable into pieces of 1 to 30 mm;
b) blanching the vegetable pieces at a temperature of 60 to 90° C.;
c) contacting the blanched vegetable pieces with a macerating enzyme activity;
d) blending the macerated vegetable pieces and obtaining a puree. The examples of the international patent application describe the preparation of carrot puree using this methodology.

Broxterman et al. (*Acetylated pectins in raw and heat processed carrot*, Carbohydrate Polymers 177 (2017) 58-66) describe a study in which the effect of heat processing on pectin was studied. Water soluble solids (WSS) were extracted from an alcohol insoluble solids fraction that had been isolated from peeled carrots or heat treated carrot cubes. In order to study the fine chemical structure of pectin, controlled degradation by pectolytic enzymes was performed. WSS was degraded by polygalacturonase (endo-PG) from *A. aculeatus* and pectin lyase (PL) from *A. niger_*

SUMMARY OF THE INVENTION

The inventors have discovered that the effectiveness of carrot RG-I polysaccharides against infections can be substantially improved by enzymatically hydrolysing the RG-I polysaccharides to remove at least part of the homogalacturonan component. The enzymatically hydrolysed carrot RG-I polysaccharides of the present invention are characterised by the following combination of features:
a molecular weight in the range 10-300 kDa;
a backbone consisting of galacturonic acid residues and rhamnose residues, said rhamnose residues being contained in alpha(1→4)-galacturonic-alpha(1→2)-rhamnose residues;
the following monosaccharide composition:
20-60 mol. % galacturonic acid residues, wherein the individual galacturonic acids can be methylated and/or acetyl-esterified;
8-50 mol. % rhamnose residues;
0-40 mol. % arabinose residues;
0-40 mol. % galactose residues;
molar ratio of galacturonic acid residues to rhamnose residues in the range of 5:1 to 1:1;
galacturonic acid residues, rhamnose residues, arabinose residues and galactose residues together constitute at least 85 mol. % of the monosaccharide residues in the carrot RG-I polysaccharides.

One aspect of the invention relates to the use of a product containing the aforementioned carrot RG-I polysaccharides in therapeutic or prophylactic treatment of infections.

Although the inventors do not wish to be bound by theory, it is believed that the removal of the homogalacturonan component (lowering the [GalA]:[Rha] ratio) alters the physicochemical properties of the RG-I polysaccharide, resulting in three-dimensional configurations of the molecule that interact more effectively with so-called pattern recognition receptors in the intestinal tract and on human Peripheral Blood Mononuclear Cells. It is believed that interaction of RG-I polysaccharide with pattern recognition receptors expressed on epithelial cells and other immunologically active cells can modulate their functional responsiveness, which through production of mediators and recirculation of immunologically active cells can improve resistance to infections in the intestinal tract as well as at other sites in the body including the oral cavity, the respiratory tract, the urinary tract, the vagina and the skin.

The use of pectolytic enzymes to remove homogalacturonan elements offers the advantage that it provides a cost-effective way of increasing the yield of immunomodulatory RG-I polysaccharide.

Another aspect of the invention relates to a product selected from a nutritional formulation, a food product, a dietary supplement, a beverage and a pharmaceutical product, said product containing at least 0.1% by weight of dry matter of the carrot RG-I polysaccharides as described above, and wherein the carrot RG-I polysaccharides represent at least 20 wt. % of the pectic polysaccharides present in the product, said pectic polysaccharides being defined as optionally branched polysaccharides having a molecular weight larger than 10 kDa and comprising a backbone that consists of galacturonic acid residues and rhamnose residues, said rhamnose residues being contained in alpha (1→4)-galacturonic-alpha(1→2)-rhamnose residues.

The enzymatically hydrolysed carrot RG-I polysaccharides of the present invention can be produced by a process comprising:
  providing a pectin isolate from carrot (e.g. carrot pomace), said isolate comprising at least 5% by weight of dry matter of pectic polysaccharides having a molecular weight of at least 15 kDa and having a backbone consisting of galacturonic acid residues and rhamnose residues, said rhamnose residues being contained in alpha(1→4)-galacturonic-alpha(1→2)-rhamnose residues;
  partially hydrolysing said pectic polysaccharides using one or more galacturonases selected from pectin lyase (EC 4.2.2.10), pectate lyase (EC 4.2.2.2), endo-polygalacturonase (EC 3.2.1.15), exopolygalacturonase (EC 3.2.1.67 and EC 3.2.1.82); and
  subjecting the partially hydrolysed pectic polysaccharides to a solid-liquid separation technique selected from centrifugation, decanting, filtration and combinations thereof to produce a liquid fraction containing partially hydrolysed pectic polysaccharides;
  subjecting the liquid fraction to ultrafiltration using an ultrafiltration membrane having a molecular weight cut-off in the range of 10 to 100 kDa; and
  recovering a retentate containing the partially hydrolysed pectic polysaccharides.

DETAILED DESCRIPTION OF THE INVENTION

Accordingly, a first aspect of the invention relates to a product for use in the therapeutic or prophylactic treatment of infections, said treatment comprising oral administration of the product, wherein the product is selected from a nutritional formulation, a food product, a dietary supplement, a beverage and a pharmaceutical product, said product containing at least 0.1% by weight of dry matter of carrot RG-I polysaccharides having the following combination features:
  a molecular weight in the range 10-300 kDa;
  a backbone consisting of galacturonic acid residues and rhamnose residues, said rhamnose residues being contained in alpha(1→4)-galacturonic-alpha(1→2)-rhamnose residues;
  the following monosaccharide composition:
    20-60 mol. % galacturonic acid residues, wherein the individual galacturonic acids can be methylated at the C-6 position and/or acetylated at the O-2 and/or the O-3 position;
    8-50 mol. % rhamnose residues;
    0-40 mol. % arabinose residues;
    0-40 mol. % galactose residues;
    molar ratio of galacturonic acid residues to rhamnose residues in the range of 5:1 to 1:1;
    galacturonic acid residues, rhamnose residues, arabinose residues and galactose residues together constitute at least 85 mol. % of the monosaccharide residues in the carrot RG-I polysaccharides.

The term "branched polysaccharide" as used herein refers to a polysaccharide comprising a linear backbone chain of monosaccharide units bound together by glycosidic linkages, wherein at least one of the monosaccharide units within the backbone chain carries a sidechain of one or more glycosidically linked monosaccharide units.

The terms "backbone chain" and "backbone" are synonyms.

The term "pectic polysaccharide" as used herein refers to optionally branched polysaccharides having a molecular weight larger than 10 kDa and comprising a backbone that consists of galacturonic acid residues and rhamnose residues, said rhamnose residues being contained in alpha (1→4)-galacturonic-alpha(1→2)-rhamnose residues.

The term "stretch" as used herein refers to a sequence of two glycosidically linked monosaccharide units within the backbone of a polysaccharide, excluding any sidechains that are attached thereto.

The term "domain" as used herein refers to a stretch plus any sidechains that are attached to said stretch.

The term "rhamnogalacturonan-I stretch" or "RG-I stretch" refers to a stretch consisting of galacturonic acid (GalA) and rhamnose (Rha) pairs, wherein the GalA residues are linked to the Rha residues via the 1 and 4 positions, while the Rha residues are linked to the GalA residue via the anomeric and 2-OH positions, i.e. alternating alpha(1→4)-galacturonic-alpha(1→2)-rhamnose residues. The RG-I domain can comprise side chains such as, for example galactan, arabinan and arabinogalactan side chains.

The term "rhamnogalacturonan-I polysaccharide" or "RG-I polysaccharide" refers to optionally branched pectic polysaccharides that comprise a backbone that contains one or more rhamnogalacturonan-I stretches.

The term "alpha(1,4)-linked galacturonic acid stretch" refers to a stretch consisting of alpha(1→4)-galacturonic residues.

Besides RG-I domains, the carrot RG-I polysaccharides of the present invention may contain one or more of the following domains:
homogalacturonan (HG),
xylogalacturonan (XG),
apiogalacturonan (AG)
rhamnogalacturonan-II (RG-II).

The domains XG, AG and RG-II typically represent only a minor fraction of the RG-I polysaccharides.

The HG domains, XG domains, AG and RG-II domains that are optionally present in the RG-I polysaccharides of the present invention comprise a backbone that consists of a linear chain of two or more α-(1→4)-linked D-galacturonic acids.

HG domains do not contain any sidechains. The carboxyl groups of galacturonic acid residues within the backbone of HG domains may be esterified. Esterified galacturonic acid may occur in the form of the methyl ester or acetyl ester.

The backbone of XG domains contains one or more sidechains in the form of D-xylose.

The backbone of AG domains contains one or more sidechains that are composed of one or more D-apiose residues.

The backbone of RG-II contains one or more side chains that are not exclusively composed of D-xylose or D-apiose. The carboxyl groups of galacturonic acid residues within the backbone of RG-II domains may be esterified. Galacturonic acid may be esterified either by methyl or acetyl groups, forming methyl or acetyl esters, respectively.

The terminology "degree of acetylation" refers to the number of acetyl residues per galacturonic acid residue, expressed as a percentage.

The terminology "degree of methylation" refers to the number of methyl residues per galacturonic acid residue, expressed as a percentage.

The concentration of different polysaccharides and their monosaccharide composition can be determined by analytical techniques known to the skilled person. After acid hydrolysis (methanolysis), the monosaccharide composition of neutral sugars, can suitably be determined by High Performance Anion Exchange Chromatography combined with Pulse Amperometric Detection (HPAEC-PAD).

Uronic acids (Galacturonic acid being the dominant form of uronic acids) can be determined using the colorimetric m-hydroxydiphenyl assay.

The molecular size distribution can be determined by High Performance Size-Exclusion Chromatography using refractive index (RI) detection (concentration).

The above mentioned analytical methods are described in: Analytical Biochemistry Vol. 207, Issue 1, 1992, pg 176 (for neutral sugar analysis) and in Mol. Nutr. Food Res., Vol 61, Issue 1, 2017, 1600243 (for the Uronic acid analysis and the molecular size distribution).

All percentages mentioned herein, unless otherwise stated, refer to the percentage by weight.

Oral administration within the context of the present treatment encompasses self-administration.

The use in therapeutic or prophylactic treatment according to the invention preferably comprises oral administration of the product in a dose providing at least 100 mg, more preferably at least 350 mg and most preferably 350-5000 mg of the carrot RG-I polysaccharides.

In another preferred embodiment, the treatment comprises oral administration of the product product in a daily dose providing at least 100 mg, more preferably at least 350 mg and most preferably 350-5000 mg of the carrot RG-I polysaccharides According to a particularly preferred embodiment, the product is used for the therapeutic or prophylactic treatment of infections of the upper respiratory tract, such as a cold or flu.

According to another preferred embodiment, the product is used for the therapeutic or prophylactic treatment of infections of the intestinal tract, such as gastroenteritis.

The subject to which the RG-I polysaccharides containing composition of the present invention is orally administered preferably is a mammal, more preferably a human subject.

The product of the present invention preferably is a nutritional formulation, a food product, a dietary supplement or a beverage.

The product preferably contains at least 0.2% by weight of dry matter, more preferably 0.3-10% by weight of dry matter and most preferably 0.4-5% by weight of dry matter of the carrot RG-I polysaccharides.

The carrot RG-I polysaccharides are preferably incorporated in the product of the present invention in the form of an pectic polysaccharide isolate that is enriched in RG-I polysaccharides. Accordingly, in a particularly preferred embodiment, the carrot RG-I polysaccharides represent at least 20 wt. %, more preferably at least 30 wt. %, even more preferably 60 wt. %, and most preferably at least 80 wt. % of the pectic polysaccharides present in the product, said pectic polysaccharides being defined as optionally branched polysaccharides having a molecular weight in excess of 10 kDa and comprising a backbone that consists of galacturonic acid residues and rhamnose residues, said rhamnose residues being contained in alpha(1→4)-galacturonic-alpha(1→2)-rhamnose residues.

The carrot RG-I polysaccharides that are employed in accordance with the present invention have a backbone that comprises rhamnogalacturonan-I stretches and optionally alpha(1,4)-linked homo-galacturonic acid stretches. The molar ratio of galacturonic acid residues to rhamnose residues in the carrot RG-I polysaccharides is within the range of 5:1 to 1:1. Preferably the molar ratio of galacturonic acid residues to rhamnose residues in the carrot RG-I polysaccharides ranges from 4.8:1 to 1:1, more preferably from 4.5:1 to 1:1, even more preferably from 4.2:1 to 1:1, most preferably from 4:1 to 1.1:1.

Rhamnose residues typically represent 9-45%, more preferably 10-40% and most preferably 11-35% of all the monosaccharide residues contained in the carrot RG-I polysaccharides, i.e. including the monosaccharide residues that are contained in sidechains.

Galacturonic acid residues typically represent 21-55%, more preferably 22-50% and most preferably 23-45% of all the monosaccharide residues contained in the carrot RG-I polysaccharides, i.e. including the monosaccharide residues that are contained in sidechains.

Arabinose residues typically represent 4-38%, more preferably 6-36% and most preferably 8-34% of all the monosaccharide residues contained in the carrot RG-I polysaccharides.

Galactose residues typically represent 4-42%, more preferably 8-40% and most preferably 10-38% of all the monosaccharide residues contained in the carrot RG-I polysaccharides.

The combination of galacturonic acid residues, rhamnose residues, arabinose residues and galactose residues together preferably constitutes at least 88 mol. %, more preferably at least 90 mol. % and most preferably at least 92 mol. % of the monosaccharide residues in the carrot RG-I polysaccharides.

The carrot RG-I polysaccharides typically have a molecular weight of at least 10 kDa. More preferably, the one or more RG-I polysaccharides have a molecular weight between 20 kDa and 300 kDa, most preferably between 40 kDa and 300 kDa.

The carrot RG-I polysaccharides of the present invention can suitably be produced by enzymatic hydrolysis of pectic polysaccharides that are found in carrot. Pectic polysaccharides found in carrot typically have a degree of acetylation of 30-50% and a degree of methylation of 60-80%. Removal of homogalacturonan (HG) domains form these pectic polysaccharides by enzymatic hydrolysis typically yields a RG-I enriched polysaccharide having a reduced degree of methylation and an increased degree of acetylation.

The inventors have found that the enzymatic hydrolysis that is employed in accordance with the present invention typically yields carrot RG-I polysaccharides having a degree of acetylation of at least 20%, more preferably of 30-110%, even preferably of 35-90% and most preferably of 40-70%.

In accordance with a preferred embodiment of the present invention, the enzymatic preparation of the carrot RG-I polysaccharides results in a substantial reduction of the degree of methylation, e.g. due to pectinesterase activity. Preferably, the carrot RG-I polysaccharides have a degree of methylation of not more than 50%, more preferably of not more than 40% and most preferably of 10-30%.

According to another preferred embodiment, the ratio of the degree of acetylation (DA) of the carrot RG-I polysaccharides to the degree of methylation (DM) of the carrot RG-I polysaccharides preferably is 1 or more, more preferably 2 or more, more preferably 3 or more, and most preferably 5 or more. Since pectinesterase activity does not have a significant impact on the degree of acetylation of the enzymatically prepared carrot RG-I polysaccharides, RG-I polysaccharides having a very high DA:DM ratio can be obtained by partially hydrolysing carrot pectic polysaccharides using a combination of pectinase (polygalacturonase and/or lyase) and pectinesterase.

In accordance with another preferred embodiment, the enzymatic preparation of the carrot RG-I polysaccharides from pectic polysaccharides yields carrot RG-I polysaccharides that contain an unsaturated galacturonic acid residue at the terminus. Pectic polysaccharides found in carrot normally do not contain unsaturated galacturonic acid residues. However, hydrolysis of these pectic polysaccharides by pectin lyase and/or pectate lyase, inevitably yields polysaccharide fragments that contain a terminal unsaturated non-reducing galacturonic acid residue. Preferably, at least 10%, more preferably at least 25% and most preferably at least 50% of the terminal non-reducing galacuturonic acid residues in the RG-I polysaccharides are unsaturated galacturonic acid residues. Unsaturated galacturonic acids can easily be identified, e.g. by measuring UV absorption at 235 nm.

The backbone of the carrot RG-I polysaccharides can comprise one or more side chains. These sidechains may contain residues of arabinose and/or galactose, and minor amounts of residues of the monomers fucose, glucose, glucuronic acid, xylose, and/or uronic acid. The one or more side chains preferably are selected from galactan side chains, arabinan side chains and arabinogalactan side chains.

The arabinan side chain comprises at least one or more alpha(1,5)-linked arabinose residues and is substituted to the 4-OH position of a rhamnose residues in the RG-I domain. The arabinan side chain may be linear or branched. In case the side chain is linear, the side chain consists of alpha(1, 5)-linked arabinose residues. In case the arabinan side chain is a branched side chain, one or more alpha-arabinose residues are linked to the O-2 and/or O-3 of alpha(1,5)-linked arabinoses.

The galactan side chain comprises at least one or more beta(1,4)-linked galactose residues and is substituted at the O-4 position of a rhamnose residues in the RG-I domain.

The arabinogalactan side chain is substituted at the O-4 position of a rhamnose residue in the RG-I domain and can be a type I arabinogalactan (AGI) or a type II arabinogalactan (AGII). AGI is composed of a (1→4)-β-D-Galp backbone on which substitutions by monomeric Galp units at the O-6 or at the O-3 position can occur. AGI is further substituted with α-L-Araf-p residues and/or with (1→5)-α-L-Araf short side chains. AGII is composed of α(1→3)-β-D-Galp backbone decorated with (1→6)-β-D-Galp secondary chains, which are arabinosylated.

Preferably, arabinose residues and rhamnose residues are present in the carrot RG-I polysaccharides in a molar ratio of less than 4:1, more preferably of less than 3:1, most preferably of less than 2:1.

Galactose residues and rhamnose residues are preferably present in the carrot RG-I polysaccharides in a molar ratio of less than 4:1, more preferably of less than 3.2:1, most preferably of less than 2.5:1.

The molar ratio of the combination of arabinose residues and galactose residues to rhamnose residues in the carrot RG-I polysaccharides preferably is less than 7:1, more preferably less than 5:1 and most preferably less than 4:1.

The combination of galacturonic acid residues and rhamnose residues preferably constitutes at least 30 mol. %, more preferably 35-90 mol. % and most preferably 40-75 mol. % of the monosaccharide residues contained in the carrot RG-I polysaccharides.

According to a particularly preferred embodiment, the carrot RG-I polysaccharides have the following monosaccharide composition:
- 21-55 mol. % galacturonic acid residues, wherein the individual galacturonic acids can be methylated and/or acetyl-esterified;
- 9-35 mol. % rhamnose residues;
- 5-35 mol. % arabinose residues;
- 5-40 mol. % galactose residues.

The carrot RG-I polysaccharides in the product of the present invention are preferably obtained by partial enzymatic hydrolysis of carrot pectin. According to a particularly preferred embodiment, the carrot RG-I polysaccharides are obtained by enzymatic hydrolysis of carrot pectin using one or more pectinases selected from pectin lyase (EC 4.2.2.10), pectate lyase (EC 4.2.2.2), endo-polygalacturonase (EC 3.2.1.15), exopolygalacturonase (EC 3.2.1.67 and EC 3.2.1.82). Most preferably, the carrot RG-I polysaccharides are obtained by enzymatic hydrolysis of carrot pectin using one or more pectinases selected from pectin lyase (EC 4.2.2.10) and endo-polygalacturonase (EC 3.2.1.15).

The product of the present invention preferably contains traces of one or more of the aforementioned pectinases. These pectinases may be present in the product in active and/or inactive form.

According to one preferred embodiment, the carrot RG-I polysaccharides are obtained by enzymatic hydrolysis of carrot pectin using endopolygalacturonase and/or exopolygalacturonase in combination with pectinesterase (EC 3.1.1.11).

According to another preferred embodiment, the carrot RG-I polysaccharides are obtained by enzymatic hydrolysis of carrot pectin using pectin lyase and/or pectate lyase.

Besides the carrot RG-I polysaccharides, the product of the present invention preferably contains at least 1% by weight of dry matter, more preferably at least 3% by weight of dry matter of one or more prebiotics selected from lactulose, inuline, fructooligosaccharides, galactooligosaccharides, milk oligosaccharides, guar gum and gum Arabic. Even more preferably, the product contains at least 1% by weight of dry matter, more preferably at least 3% by weight of dry matter of one or more prebiotics selected from lactulose, inuline, fructooligosaccharides, galactooligosaccharides and milk oligosaccharides.

Another aspect of the invention relates to a product selected from a nutritional formulation, a food product, a dietary supplement, a beverage and a pharmaceutical product, said product containing at least 0.1% by weight of dry matter of carrot RG-I polysaccharides as described above; wherein the carrot RG-I polysaccharides represent at least 20 wt. % of the pectic polysaccharides present in the product, said pectic polysaccharides being defined as optionally branched polysaccharides having a molecular weight larger than 10 kDa and comprising a backbone that consists of galacturonic acid residues and rhamnose residues, said rhamnose residues being contained in alpha(1→4)-galacturonic-alpha(1→2)-rhamnose residues.

Yet another aspect of the present invention relates to a process of preparing carrot RG-I polysaccharides, said process comprising:
  providing a pectin isolate from carrot, said isolate comprising at least 5% by weight of dry matter, preferably at least 10% by weight of dry matter, more preferably at least 25% by weight of dry matter of pectic polysaccharides having a molecular weight of at least 15 kDa and having a backbone consisting of galacturonic acid residues and rhamnose residues, said rhamnose residues being contained in alpha(1→4)-galacturonic-alpha(1→2)-rhamnose residues;
  partially hydrolysing said pectic polysaccharides using one or more pectinases selected from pectin lyase (EC 4.2.2.10), pectate lyase (EC 4.2.2.2), endo-polygalacturonase (EC 3.2.1.15), exopolygalacturonase (EC 3.2.1.67 and EC 3.2.1.82),
  subjecting the partially hydrolysed pectic polysaccharides to a solid-liquid separation technique selected from centrifugation, decanting, filtration and combinations thereof to produce a liquid fraction containing partially hydrolysed pectic polysaccharides;
  subjecting the liquid fraction to ultrafiltration using an ultrafiltration membrane having a molecular weight cut-off in the range of 10 to 100 kDa; and
  recovering a retentate containing the partially hydrolysed pectic polysaccharides.

According to one preferred embodiment, the pectic polysaccharides are partially hydrolysed using one or more pectinases selected from endo-polygalacturonase (EC 3.2.1.15) and exopolygalacturonase (EC 3.2.1.67 and EC 3.2.1.82).

According to another preferred embodiment, the pectic polysaccharides are partially hydrolysed using one or more pectinases selected from pectin lyase (EC 4.2.2.10) and pectate lyase (EC 4.2.2.2). As explained herein before, hydrolysis of pectic polysaccharides by these lyases inevitably yields polysaccharide fragments that contain a terminal unsaturated non-reducing galacturonic acid residue.

The pectic polysaccharides are preferably hydrolysed in the present process using a combination of the aforementioned one or more pectinases and one or more pectinesterases (EC 3.1.1.11). The one or more pectinesterases may be employed prior to or simultaneous with the one or more pectinases. The combined use of pectinases and pectinesterases is particularly advantageous in case the pectinase employed is selected from endo-polygalacturonase, exopolygalacturonase and combinations thereof. The combined use pecintases and pectinesterases typically yields partially hydrolysed carrot pectic polysaccharides having a reduced degree of methylation and an increased acetylation/methylation ratio.

The partial hydrolysis of the pectic polysaccharides is preferably carried out by keeping an aqueous solution of the pectic polysaccharides and the pectinase at a temperature in the range of 15 to 70° C. for at least 10 minutes, preferably for 15-300 minutes.

The pectin isolate from carrot that is employed in the present process preferably is carrot pulp obtained from the production of carrot juice or a fraction of such carrot pulp.

As used herein, the term "ultrafiltration" also encompasses dialysis using an ultrafiltration membrane. In a particularly preferred embodiment of the present process, the liquid fraction that is obtained from the solid-liquid separation is subjected to ultrafiltration using an ultrafiltration membrane having a molecular weight cut-off in the range of 12 to 80 kDa. More preferably, said ultrafiltration membrane has a molecular weight cut-off in the range of 10 to 60 kDa, most preferably in the range of 20 to 45 kDa.

According to a particularly preferred embodiment, the retentate that is obtained in the ultrafiltration step is concentrated to a water content of less than 50 wt. %. Even more preferably, the retentate is dried to a water content of less than 15 wt. %, most preferably of less than 12 wt. %.

The aforementioned retentate is preferably dried using a drying technique selected from spray drying, drum drying and freeze drying. More preferably, the drying technique used is spray drying or drum drying. Most preferably, the retentate is dried by means of spray drying.

The present process preferably does not employ organic solvents.

The carrot RG-I polysaccharides obtained by the process of the present invention preferably are carrot RG-I polysaccharides as described herein before.

The present invention also provides a method of preparing a product selected from a nutritional formulation, a food product, a beverage, a dietary supplement and a pharmaceutical product, said method comprising incorporating therein 0.1-50% by weight of dry matter of the carrot RG-I polysaccharides as described herein before. The product is preferably prepared by combining the carrot RG-I polysaccharides with one or more edible ingredients.

One embodiment of the present method relates to the preparation of a product selected from nutritional formulation, a food product and a beverage, said method comprising incorporating therein 0.5-40% by weight of dry matter, more preferably 1-30% by weight of dry matter of the carrot RG-I polysaccharides.

In another embodiment, the present method is used to prepare a product selected from a dietary supplement and a pharmaceutical product, said method comprising incorporating therein 10-90% by weight of dry matter, preferably 20-80% by weight of dry matter and most preferably 30-60% by weight of dry of the carrot RG-I polysaccharides.

The carrot RG-I polysaccharides are preferably incorporated in the product in the form of an isolate containing at least 5%, more preferably at least 10%, even more preferably at least 20% and most preferably at least 30% of the carrot RG-I polysaccharides by weight of dry matter.

According to another preferred embodiment, the carrot RG-I polysaccharides are incorporated in the product in the form of a powder, preferably in the form of a powder having a water content of less than 15 wt. %, more preferably of less than 12 wt. %.

Preferably, the aforementioned powder contains less than 30 wt. %, more preferably less than 20 wt. % and most preferably less than 10 wt. % material having a molecular weight of less than 10 kDa.

The carrot RG-I polysaccharides are preferably incorporated in the product in the form of an isolate, the carrot RG-I polysaccharides representing at least 20 wt. %, more preferably at least 30 wt. %, even more preferably at least 60 wt. % and most preferably at least 80 wt. % of the pectic polysaccharides present in the isolate, said pectic polysaccharides being defined as optionally branched polysaccharides having a molecular weight larger than of 10 kDa and comprising a backbone that consists of galacturonic acid residues and rhamnose residues, said rhamnose residues being contained in alpha(1→4)-galacturonic-alpha(1→2)-rhamnose residues.

The invention is further illustrated by the following non-limiting examples.

EXAMPLES

Example 1

Dried carrot pomace (carrot fibre powder, GreendFields, Poland), the residue of carrot juice production, was dispersed in demineralised water (100 g/l) and subjected to enzymatic hydrolysis on labscale using 3 different commercial enzymes (enzymolysis conditions: 45° C., 120 minutes):
1. Pectinex® Yield Mash ex Novozymes (0.02% of total dispersion)
2. Pectinex® Ultra Mash ex Novozymes (0.02% of total dispersion)
3. Pectinex® Ultra Mash ex Novozymes (0.05% of total dispersion)

Enzymolysis was terminated by heating at 90° C. for 10 min, followed by centrifugation and dialysis of the supernatant using a membrane with a 10 kDa cut off (Microdyn Nadir; UP010).

A reference isolate was produced by introducing the dried carrot pomace in water (100 g/l), keeping the solution for 120 minutes at a temperature of 90° C., centrifugation, and dialysis of the supernatant by means of dialysis in the same way as the enzymolysed dispersions.

Example 2

The monosaccharide composition of the non-hydrolysed carrot RG-I polysaccharide of Example 1 (Reference) and of the enzymatically hydrolysed carrot RG-I polysaccharide of Example 1 (Samples 1 to 3) was determined as follows:

The concentration of different polysaccharides and their monosaccharide composition were determined using the analytical methods described in: Analytical Biochemistry Vol. 207, Issue 1, 1992, pg 176 (neutral sugar analysis) and in Mol. Nutr. Food Res., Vol 61, Issue 1, 2017, 1600243 (uronic acid analysis and molecular size distribution).

The results of the monosaccharide analysis are shown in Table 1 (Rha=rhamnose; GalA=galacturonic acid; Ara=arabinose; Gal=galactose.

TABLE 1

| Sample | Mol. % Rha | Mol. % GalA | Mol. % Ara | Mol. % Gal | [GalA]:[Rha] | [Gal]:[Rha] | [Ara]:[Rha] |
| --- | --- | --- | --- | --- | --- | --- | --- |
| Reference | 6 | 62 | 14 | 16 | 10.3 | 2.7 | 2.3 |
| 1 | 10 | 45 | 19 | 23 | 4.6 | 2.3 | 2.0 |
| 2 | 17 | 35 | 28 | 16 | 2.1 | 1.0 | 1.6 |
| 3 | 13 | 47 | 23 | 15 | 3.7 | 1.2 | 1.8 |

Example 3

The immunomodulating activity of the non-hydrolysed carrot RG-I polysaccharides of Example 1 (Reference) and of the enzymatically hydrolysed carrot RG-I polysaccharides of Example 1 (Samples 1 to 3) was determined using a human peripheral blood mononuclear cells (PBMC) assay.

Immuno Modulation Assay.

To assess the effect of the polysaccharide materials on immune function they were incubated with freshly isolated Peripheral Blood Mononuclear Cells (PBMC). In brief, PBMC were isolated from buffy coats of blood using Ficoll-plaque (Amersham). PBMC (2*10E6 cells/mL) were incubated in RPMI medium (Gibco™ RPMI 1640 Medium) with 300 µg RG-I polysaccharides for 20 hr (5% $CO_2$, 37° C.). Subsequently, supernatants were harvested and cytokines were measured using a bead array (CBA human inflammation kit, BD-Bioscience) measured on a flowcytometer (BD FACSCANTO II) according to the manufacturer's instructions. RPMI was used as negative control and LPS (from *E. coli*—Sigma L3012-5 mG) as reference to which the results were normalized with LPS as 100%. Data are expressed as % normalized to the response induced by LPS, averaged over 3 different donors for 4 different cytokines and their sum.

Table 2 shows the results of the immunomodulation assay

TABLE 2

| Sample | TNF | IL10 | IL6 | IL1B | Sum |
| --- | --- | --- | --- | --- | --- |
| Reference | 23 | 6 | 22 | 17 | 69 |
| 1 | 200 | 68 | 91 | 81 | 441 |
| 2 | 367 | 106 | 142 | 214 | 828 |
| 3 | 435 | 124 | 124 | 150 | 832 |

Example 4

Example 1 was repeated on different scales, i.e. at 20 liters (sample 1), 5,000 liters (sample 2) and 10,000 litres (sample 3), using the enzyme Pectinex® Ultra Mash ex Novozymes (conditions: 0.1% w/w of total dispersion, 45° C., 2 hrs, enzyme inactivation: 90° C. for 10 min). In samples 2 and 3, instead of centrifugation, decanting was used to separate the solids from the liquid. The supernatant was subjected to ultrafiltration, using a 10 kDa membrane, to remove small molecular components.

The monosaccharide composition of the hydrolysed polysaccharide materials was analysed suing the methods described in Example 2.

The results of the analyses are shown in Table 3.

TABLE 3

| Sample | Mol. % Rha | Mol. % GalA | Mol. % Ara | Mol. % Gal | [GalA]:[Rha] | [Gal]:[Rha] | [Ara]:[Rha] |
|---|---|---|---|---|---|---|---|
| 1 | 17 | 28 | 30 | 22 | 1.6 | 1.3 | 1.7 |
| 2 | 17 | 23 | 33 | 20 | 1.4 | 1.2 | 2.0 |
| 3 | 15 | 28 | 29 | 19 | 1.8 | 1.2 | 1.9 |

The degree of acetylation and methylation was determined as follows: Polysaccharide samples (2-5 mg) were treated with sodium hydroxide (0.1 M, overnight, 20° C.). Released methanol was measured using head-space GC equipped with a DB-WAX ETR column, Cryo Focus-4 cold trap and FID detection (adapted from Huisman et al., Food Hydrocolloids, 18, 4, 2004, 665-668)

The samples were neutralized (1 M HCl) and then the released acetyl was quantified using HPLC equipped with an Aminex HPX 87H column with guard column and RI detection (adapted from Voragen et al. Food Hydrocolloids, 1, 1, 1986, 65-70). Degree of esterification is expressed as molar amount of methanol and acetic acid released as percentage of the amount of uronic acid.

The results of the degree of esterification analyses are shown in Table 4.

TABLE 4

| | DM %[1] | DA %[2] | DA:DM |
|---|---|---|---|
| 2 | 16 | 42 | 2.6 |
| 3 | 21 | 36 | 1.7 |

[1] degree of methylation
[2] degree of acetylation

Example 5

The immunomodulating activity of the enzymatically hydrolysed carrot RG-I polysaccharides of Example 4 (Samples 1 to 3) was determined using a human peripheral blood mononuclear cells (PBMC) assay as described for Example 3. The results are shown in table 5.

TABLE 5

| | TNF | IL10 | IL6 | IL1B | Sum |
|---|---|---|---|---|---|
| 1 | 131 | 61 | 105 | 72 | 368 |
| 2 | 181 | 70 | 124 | 136 | 511 |
| 3 | 107 | 35 | 97 | 72 | 311 |

Example 6

The hydrolysed polysaccharide material of sample 2 of Example 4 was further hydrolysed, followed by isolation of a high molecular weight fraction. The polysaccharide material was dissolved in demineralised water (100 g/l) and subjected to further enzymatic hydrolysis (Pectinex® Ultra Mash ex Novozymes, 45° C., 14 hours). Enzymolysis was terminated by heating to 90° C. for 10 min.

A portion of the enzymolysed polysaccharide solutions was subjected to fractionation using semi-preparative size-exclusion chromatography to produce a fraction containing polysaccharides having a molecular weight of more than 70 kDa.

The monosaccharide composition of the non-fractionated hydrolysed polysaccharide and of the isolated high molecular fraction was analysed using the methodology described for Example 2.

The results of the analyses are shown in Table 6.

TABLE 6

| | Mol. % Rha | Mol. % GalA | Mol. % Ara | Mol. % Gal | [GalA]:[Rha] | [Ara]:[Rha] | [Gal]:[Rha] |
|---|---|---|---|---|---|---|---|
| Non fractionated | 23 | 31 | 14 | 19 | 1.3 | 0.6 | 0.8 |
| >70 kDa | 15 | 23 | 17 | 38 | 1.5 | 1.1 | 2.5 |

The immunomodulating activity of the enzymolysed polysaccharide and the high molecular fraction thereof was determined using the methodology described in Example 3. The results are shown in Table 7.

TABLE 7

| 14 hrs enzymolysis | TNF | IL10 | IL6 | IL1B | Sum of All |
|---|---|---|---|---|---|
| Non-fractionated | 295 | 95 | 130 | 158 | 678 |
| >70 kDa fraction | 302 | 112 | 139 | 174 | 726 |

Example 7

Hydrolysed pectic polysaccharide isolates were prepared by dispersing carrot pomace in water (100 g/L).

Sample 1 was extracted at 90° C. for 120 minutes without added enzyme (extract yield: 4.8%)

Sample 2 was extracted by adding Rapidase C600 (an enzyme mix containing pectin lyase, polygalacturonase, pectin esterase, cellulase and hemicellulase activity, Militz, H. Wood Sci. Technol. (1993) 28:9) with enzyme concentration at 1 g/100 mL of total dispersion, at 45° C., for 120 minutes. Enzymolysis was terminated by heating at 100° C. for 10 min (extract yield: 5.6%)

Both samples were subsequently centrifugated (18.000 g, 10 min) and the supernatant was extensively dialysed using a membrane with a 12-14 kDa (Visking, London, UK) cut off. After ultra-filtration/diafiltration the isolate was freeze-dried using a lab-scale freeze dryer.

Figure 3:
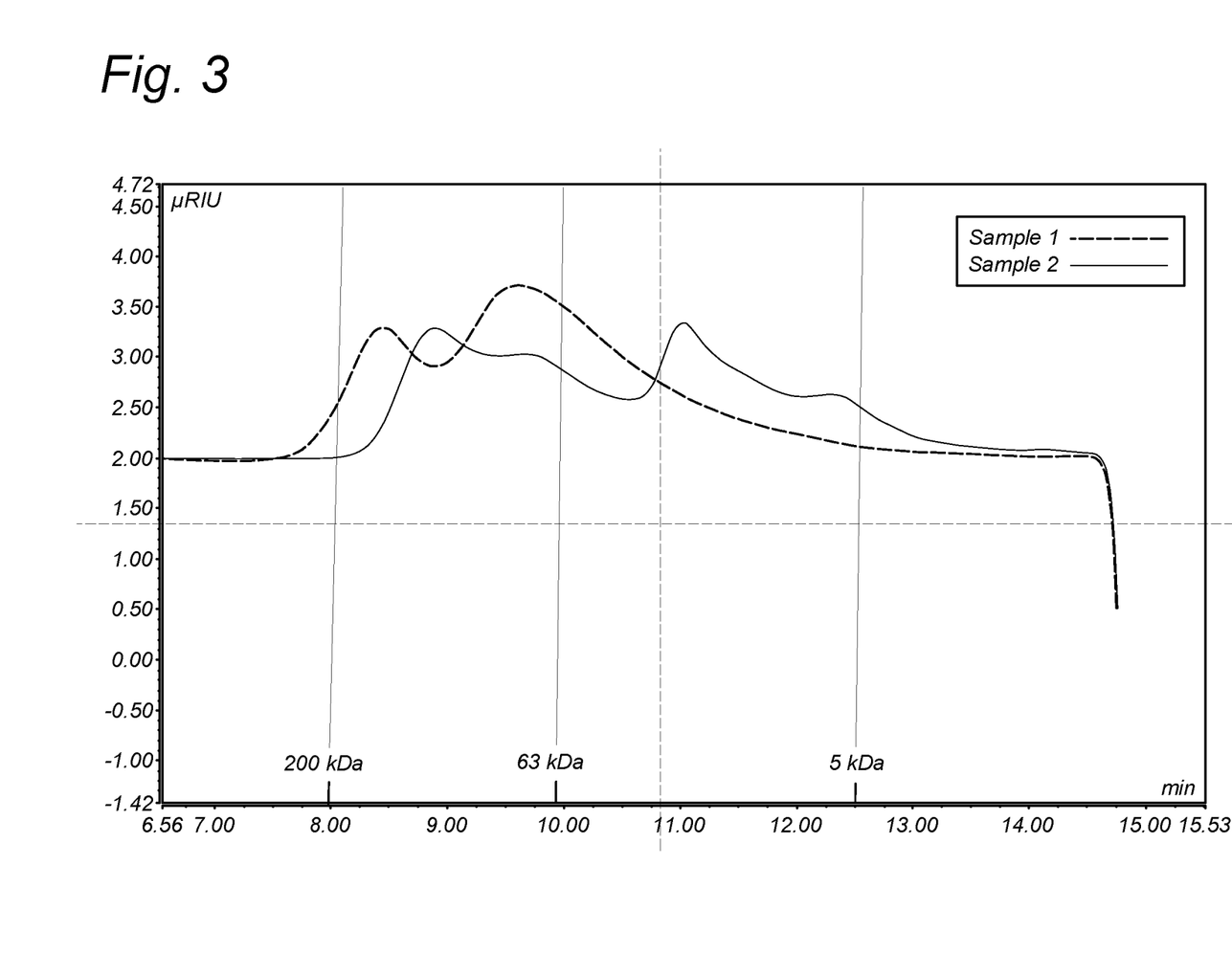
FIG. 3 shows the molecular size distribution of two hydrolysed pectic polysaccharide samples according to Example 7, as determined by HPSEC with refractive index detection.

The molecular size distribution of Sample 1 and Sample 2, as determined by HPSEC with refractive index detection, is shown in FIG. 3.

The monosaccharide composition of the two samples was analysed using the methodology described for Example 2. The results of the analyses are shown in Table 8.

TABLE 8

|  | Mol. % Rha | Mol. % GalA | Mol. % Ara | Mol. % Gal | [GalA]:[Rha] | [Ara]:[Rha] | [Gal]:[Rha] |
|---|---|---|---|---|---|---|---|
| Sample 1 | 3.7 | 47.5 | 8.0 | 11.5 | 12.8 | 3.1 | 2.2 |
| Sample 2 | 8.4 | 34.7 | 7.3 | 12.2 | 4.1 | 1.5 | 0.9 |

The invention claimed is:

1. A method of treating or reducing the risk of developing infections, comprising orally administering to a subject a product selected from the group consisting of a nutritional formulation, a food product, a dietary supplement, a beverage and a pharmaceutical product, the product comprising at least 0.1%, by weight of dry matter, carrot RG-I polysaccharides having:
   (a) a molecular weight in the range 10-300 kDa;
   (b) a backbone consisting of galacturonic acid residues and rhamnose residues, wherein the rhamnose residues are contained in alpha(1→4)-galacturonic-alpha(1→2)-rhamnose residues; the RG-I polysaccharides having a degree of methylation of not more than 50% and a degree of acetylation of more than 30%;
   (c) the following monosaccharide composition:
      (i) 20-60 mol. % galacturonic acid residues, which can be methylated at the C-6 position and/or acetylated at the O-2 and/or the O-3 position;
      (ii) 8-50 mol. % rhamnose residues;
      (iii) 0-40 mol. % arabinose residues;
      (iv) 0-45 mol. % galactose residues;
      (v) a molar ratio of galacturonic acid residues to rhamnose residues in the range of 5:1 to 1:1;
      (vi) galacturonic acid residues, rhamnose residues, arabinose residues and galactose residues together constituting at least 85 mol. % of the monosaccharide residues in the carrot RG-I polysaccharides.

2. The method according to claim 1, wherein the ratio of the degree of acetylation of the carrot RG-I polysaccharides to the degree of methylation of the carrot RG-I polysaccharides is 1 or more.

3. The method according to claim 1, wherein at least 10% of terminal non-reducing galacturonic acid residues in the RG-I polysaccharides are unsaturated galacturonic acid residues.

4. The method according to claim 1, wherein the carrot RG-I polysaccharides represent at least 20 wt. % of pectic polysaccharides present in the product, wherein the pectic polysaccharides are defined as optionally branched polysaccharides having a molecular weight larger than 10 kDa and comprising a backbone that consists of galacturonic acid residues and rhamnose residues, said rhamnose residues being contained in alpha(1→4)-galacturonic-alpha(1→2)-rhamnose residues.

5. The method according to claim 1, wherein the molar ratio of the combination of arabinose residues and galactose residues to rhamnose residues in the carrot RG-I polysaccharides is less than 5:1.

6. The method according to claim 5, wherein the molar ratio of the combination of arabinose residues and galactose residues to rhamnose residues in the carrot RG-I polysaccharides is less than 4.5:1.

7. The method according to claim 1, wherein the carrot RG-I polysaccharides have the following monosaccharide composition:
   (i) 21-55 mol. % galacturonic acid residues, wherein the individual galacturonic acids can be methylated and/or acetyl-esterified;
   (ii) 9-35 mol. % rhamnose residues;
   (iii) 5-40 mol. % arabinose residues;
   (iv) 5-40 mol. % galactose residues.

8. The method according to claim 1, wherein the carrot RG-I polysaccharides have been obtained by partial enzymatic hydrolysis of carrot pectin.

9. The method according to claim 1, wherein the product is administered in a dose providing at least 200 mg of the carrot RG-I polysaccharides.

* * * * *